United States Patent [19]
Fischer et al.

[11] 4,056,471
[45] Nov. 1, 1977

[54] ADSORPTION ARRANGEMENT

[75] Inventors: Paul Fischer, Regensdorf; Edward Wisz, Kaiseraugst, both of Switzerland

[73] Assignee: Chemische Fabrik Uetikon, Uetikon, Switzerland

[21] Appl. No.: 404,603

[22] Filed: Oct. 9, 1973

[30] Foreign Application Priority Data

Oct. 13, 1972 Switzerland ............... 14984/72

[51] Int. Cl.² ............................................. B01D 35/18
[52] U.S. Cl. .................................... 210/186; 210/269
[58] Field of Search .................. 210/30, 32, 34, 35, 210/41, 71, 175, 181, 185, 186, 269; 252/411 R

[56] References Cited

U.S. PATENT DOCUMENTS

| 1,866,417 | 7/1932 | Mackert | 210/32 |
| 2,323,524 | 7/1943 | Downs | 210/32 |
| 3,224,845 | 12/1965 | Thomas | 210/41 |
| 3,448,042 | 6/1969 | Mattia et al. | 210/32 |
| 3,734,293 | 5/1973 | Biskis | 210/185 |

Primary Examiner—Wilbur L. Bascomb, Jr.
Assistant Examiner—Ivars Cintins
Attorney, Agent, or Firm—Michael J. Striker

[57] ABSTRACT

A liquid is contacted with an adsorption agent so that the latter adsorbs and retains the impurities in the liquid. Subsequently, a portion of the purified liquid is vaporized. The vapor is brought into contact with the adsorption agent and removes the adsorbed impurities therefrom to thereby regenerate the adsorption agent. After condensation of the vapor so as to segregate the impurities removed from the adsorption agent, the resulting liquid may again be contacted with the adsorption agent.

1 Claim, 2 Drawing Figures

ADSORPTION ARRANGEMENT

BACKGROUND OF THE INVENTION

The invention relates generally to adsorption arrangements. More particularly, the invention relates to an adsorption arrangement wherein the adsorbing agent is regenerated or reactivated.

The purification, separation or drying of fluids, especially solvent mixtures, is, in known manner, achieved by sorption of the undesired components or impurities onto microfilters or other adsorption agents such as activated alumina, activated carbon or silica gel. Subsequent to the sorption, the adsorption agent must be reactivated.

The reactivation of the adsorption agent has, in the known methods used until now, usually been carried out by conveying a gaseous substance different from the fluid purified by the adsorption agent through the latter at elevated temperature. The degree of activation achieved or, in other words, the quantity of residual impurities still adhering to the adsorption agent after the reactivation, determines the degree of purity achievable for the fluid to be purified with the adsorption agent.

Organic compounds such as, for example, solvent vapors, have a great tendency to form explosive gas mixtures when they are mixed with air and, in addition, have a great tendency to undergo coking at temperatures in excess of 200° C. The latter effect has the result that tar-like desposits form on the adsorption agent. In view of the above, the reactivation or regeneration of adsorption agents has generally been performed by using nitrogen.

For economic reasons, the nitrogen must be recirculated. During this process, the adsorbate, that is, the impurities adsorbed by the adsorption agent and which are removed therefrom by the nitrogen, are extracted or segregated from the hot nitrogen by cooling. This process exhibits various disadvantages.

Where nitrogen is used as a regenerating medium and Na-A-zeolite is used as an adsorption agent, the conditions for achieving a residual adsorbed water or moisture content of the order of 2% for the adsorption agent are, for instance, as follows:

A. Regeneration temperature 350° C Dew point of the inert gas 27° C
B. Regeneration temperature 270° C Dew point of the inert gas 2° C
C. Regeneration temperature 150° C Dew point of the inert gas −40° C The regeneration temperature for the microfilter, which latter is used for the purification of solvents, is too high in the Examples A and B given above since, as already mentioned, coking occurs at temperatures in excess of 200° C. On the other hand, the dew point of the recirculated regenerating gas in the Examples B and C above can only be obtained by using heat-exchangers in conjunction with the cooling systems.

Furthermore, since some of the fluid to be purified always remains as a component in the desorbing gas, that is, the gas used for reactivating the adsorption agent, losses are to be expected due to emissions which are very difficult to eliminate. There is also the further consideration that the danger of an explosion is not completely out of the question since the recirculating system can be sealed off only at very high expense.

Therefore, it is desirable to improve on the known methods of regenerating adsorption agents.

SUMMARY OF THE INVENTION

It is, accordingly, a general object of the invention to provide a novel arrangement whereby adsorption agents may be regenerated.

More particularly, it is an object of the invention to provide an arrangement for regenerating adsorption agents whereby the danger of explosion is substantially reduced.

Another object of the invention is to provide an arrangement for regenerating adsorption agents whereby the formation of tar-like deposits on the adsorption agent is prevented.

An additional object of the invention is to provide an arrangement for regenerating adsorption agents whereby losses of the fluid to be purified are minimized.

It is also an object of the invention to provide an arrangement for regenerating adsorption agents whereby the regeneration may be carried out economically.

With the above objects, and others which will become apparent, in view, the invention provides an adsorption arrangement for a fluid which is convertible between a liquid and a gaseous state, and wherein the adsorption agent is regenerated, which comprises contacting a fluid in one of these states with an adsorption agent so that impurities from the fluid are adsorbed and retained by the adsorption agent. A portion of the purified fluid is converted from the state in which it is contacted with the adsorption agent to the other state, e.g. from liquid to gaseous state, and the impurities adsorbed by the adsorption agent are removed therefrom, at least in part, by contacting this portion of the purified fluid with the adsorption agent.

The invention may be used for the regeneration of reactivation of adsorption agents which are utilized for the purification, particularly drying, of liquid organic compounds and mixtures of the same. The regenerating agent will then be a gas and it will be seen that the regenerating gas is, in accordance with the invention, produced from a liquid organic compound which has been purified by the adsorption agent. The adsorption agent may be of a particulate material.

Since, according to the invention, the desorbing gas, that is, the gas which removes impurities from the adsorption agent, is constituted by the vapor of a purified medium, the vapor pressure of the impurities is much lower than when a circulating inert gas is used for desorption. For example, the partial pressure of the water vapor in vaporized toluene having a moisture content of 0.003% corresponds to the partial pressure of the water vapor in inert gas having a dew point as low as −38° C. The low partial pressure of the water vapor of the desorbing gas in accordance with the invention enables the desorption to be performed at a temperature such that the adsorption agent is not adversely affected in any manner.

According to an advantageous modification of the invention, a predetermined volume of the purified medium is provided for the desorption and is so chosen that the vapor of this volume of the purified medium is sufficient to reactivate the adsorption agent. In this manner, the devices necessary for recirculating the medium may be eliminated. The quantity of desorbing or regenerating gas required is dependent upon the degree to which impurities have been adsorbed by the adsorption agent, the degree of desorption desired and the dew point of the regenerating gas. The predetermined quantity of the regenerating gas provided for the desorption amounts to a fraction of the purified medium produced.

The process for desorption of the adsorption agent with the aid of the vapor of the purified medium is applicable to adsorbates other than water also. For example, the process may be utilized for ethyl alcohol, methyl alcohol, ammonia, hydrogen sulfide, etc. whether present in substantially pure form or in the form of mixtures.

Suitable media which may be used for the desorption include, for example, aliphatic and isocylic hydrocarbons; heterocylic compounds; alcohols; ether; amines; carboxylic acids; nitriles; nitro compounds; sulfoxides; halogenated hydrocarbons and aldehydes as well as mixtures of these substances. These substances should, however, be used only when: (a) they do not react chemically with the adsorption agent; and (b) they do not undergo chemical reaction in the presence of the adsorption agent.

Examples of adsorption agents include microfilters; silica gel; activated aluminum oxide and activated carbon. Furthermore, particularly microfilters as set forth on pages 14-15, 17, 21, 25 and 26 of the publication of "Molekularsiebe" by O. Grubner, P. Jiru and M. Ralek published by VEB Deutscher Verlag der Wissenschaften Berlin (1968) may be used as adsorption agents. Thus, for instance, natural zeolites and synthetic zeolites may be used as adsorption agents with the following being especially useful:

| A-zeolite | |
|---|---|
| K-type | pore size about 3 angstroms |
| Na-type | pore size about 4 angstroms |
| Ca-type | pore size about 5 angstroms |
| X-zeolite | |
| Na-type | pore size about 10 angstroms |
| Ca-type | pore size about 9 angstroms |
| Mordenite | |
| Na-type | pore size about 7 angstroms |
| H-type | pore size about 8-9 angstroms |

The invention also provides an arrangement which is particularly, although not exclusively, adapted for carrying out the novel process. In accordance with the invention, an arrangement for the adsorption of impurities from fluids which are convertible between a liquid and a gaseous state and for the regeneration of the adsorption agent includes an adsorption agent and means for contacting a fluid in one of these states with the adsorption agent so as to permit impurities from the fluid to be adsorbed and retained by the adsorption agent. Means for converting a portion of the purified fluid from the state in which it contacts the adsorption agent to the other of its states is also provided. The converting means is adapted to communicate with or communicates with the adsorption agent so as to permit the converted portion of the purified fluid to contact the adsorption agent and at least in part remove the adsorbed impurities therefrom.

Where the fluid being purified is a liquid, the converting means will be a vapor generator or, in other words, a device capable of varporizing the liquid. The adsorption agent may be located in an adsorber or adsorption vessel and a connection is provided between the vaporizer and the adsorber. The adsorber may communicate with condensing means, that is, a cooler, which is capable of condensing the regenerating gas and/or the impurities which have been removed from the adsorption agent thereby. The cooler is provided with outlet means for the removal of condensed liquid therefrom and such outlet means may include a conduit or conduits.

A preferred form of the arrangement according to the invention resides in placing the layer or bed of adsorption agent interiorly of the vaporizer used for converting the purified medium from its liquid to its gaseous state. During the sorption, the vaporizer is automatically filled with purified medium. With the help of the heat-exchange means in the boiler or vaporizer, which heat-exchange means serves to vaporize the purified liquid medium when it is desired to desorb the adsorption agent, it is also possible to additionally cool the adsorber by cooling the medium so as to remove heat generated by the adsorption.

The volume of the cooler or condensing means, which latter serves to condense the desorption gas and/or the impurities removed from the adsorption agent thereby, may be so selected that the cooler is able to accommodate the entire mixture resulting from the desorption, that is, the mixture constituted by the desorption gas and the desorbed impurities, when both the gas and the impurities are condensed to form a liquid mixture. The liquid mixture may be treated by conventional separation methods such as, for example, phase separation, coarse segregation by fractional distillation or other suitable methods.

Generally, although not necessarily always, the temperature of the adsorption agent at the time that the desorption is to start will be lower than the condensation temperature of the desorbing gas or agent. Thus, the desorbing gas will condense on the adsorption agent until the temperature of the latter reaches the condensation temperature of the desorbing gas. The heat of condensation of the desorbing gas aids in the reactivation of the adsorption agent and the use of this heat of condensation for reactivating the adsorption agent has the result that the volume of the desorbing agent, in its liquid phase, required for the desorption is very small as compared to the volume of inert gas which would be required for the same desorption. Consequently, the desorbing agent may, already during the adsorption phase, be shunted or advanced into a holding vessel of convenient volume. On the other hand, since inert gases can be held in liquid form only with complicated equipment and at great expense, such gases will normally be in the gaseous state only and, hence, will not be able to provide the advantageous heat of condensation during desorption achievable with the invention.

During the adsorption, the adsorber is additionally indirectly heated by the purified medium.

The arrangement in accordance with the invention is particularly economical since both apparatus, that is, the adsorber and the vaporizer, are united into a single aggregate and thus require less space. In addition, only a single heat-exchanger and a single insulation means are required. Furthermore, with the arrangement according to the invention, the desorption process also proceeds in an advantageous manner. This is so because, with progressing reactivation of the adsorption agent, the level of the purified medium serving as the source of the desorption gas is lowered so that the upper portion of the heating hose or coil used for converting the purified medium from its liquid to its gaseous state becomes exposed and serves to superheat the gaseous purified medium.

Since the arrangement for carrying out the process of the invention functions at low desorption temperatures, water vapor may be used as a carrier of energy.

The desorption temperature, that is, the temperature at which adsorbed impurities are removed from the adsorption agent, and the boiling temperature of the medium being purified may be regulated the pressure in the system. Regulation of the pressure in the system may be accomplished by controlling the pressure of the vaporized purified medium used for the desorption. Since the maximum desorption temperature does not lie much above the boiling temperature of the medium being purified, as fixed by regulating the pressure in the system, no undue superheating of the vaporized medium need be feared. There is, therefore, no necessity for a safety valve in the reactivation system.

The advantages of the novel process and arrangement may be summarized as follows: By using the vapor of the treated medium for desorbing the adsorption agent which is utilized for purifying the medium, lower desorption temperatures may be achieved for obtaining the same degree of reactivation. As a result, coking and the formation of tar-like deposits on the adsorption agent are avoided.

The arrangement in accordance with the invention, which makes it possible to use a predetermined quantity of the medium being purified for desorption of the adsorption agent, provides a positive, economical, and structurally simple solution to the prior art problems and requires a minimum amount of space. The arrangement may, in simple manner, be controlled fully automatically and, since it has no moving parts, is maintenance free. It is also possible to design an arrangement according to the invention so as to be portable.

The novel features which are considered as characteristic for the invention are set forth in particular in the appended claims. The invention itself, however, both as to its construction and its method of operation together with additional objects and advantages thereof, will be best understood from the following description of specific embodiments when read in connection with the accompanying drawing.

DESCRIPTION OF THE PREFERRED EMBODIMENTS

It is noted here that the term "purify" as used throughout is intended to encompass all instances where separation of two or more components is effected. Also, although the invention is described with reference to a process wherein a liquid medium is purified and a portion of the purified liquid medium is vaporized for desorption, it will be understood that there may be occasions where the reverse will be true.

Figure 1:
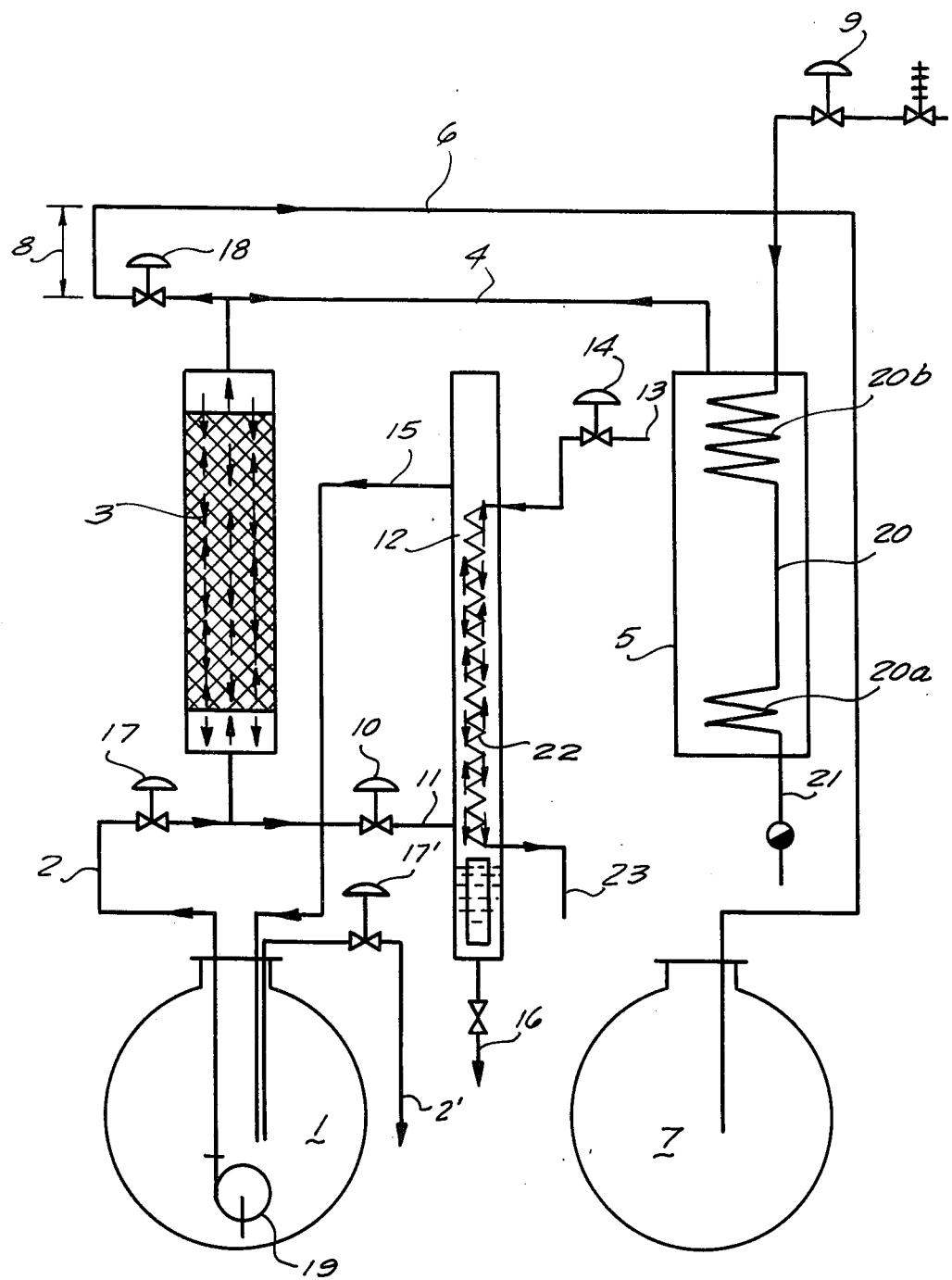
FIG. 1 is a schematic illustration of one form of arrangement for carrying out the process according to the invention.

The process according to the invention will now be described with reference to FIG. 1 of the drawing. This description will be in terms of a wet liquid medium (a moisture containing medium) which is to be dried. The wet medium is confined in a container 1 and, with the valve indicated at 10 in its closed position, the wet medium is conveyed, via a conduit 2 and through an open valve 17, into an adsorber 3 containing an adsorption agent. The direction of flow of the medium in the adsorber 3 is indicated by the upwardly pointing arrows.

The wet medium may be conveyed from the container 1 to the adsorber 3 by a pump 19 or by pressurized air. After leaving the adsorber 3, wherein at least part of the moisture is removed from the medium by adsorption, the purified liquid medium first flows into a vapor generator or converting means 5 via a conduit 4. Flow of the purified liquid medium into the vaporizer 5 continues until the latter has been filled.

After the vaporizer 5 has been filled, flow of the liquid medium through the adsorber 3 continues, although the purified or dried medium now flows through an open valve 18 and along a conduit 6 to a vessel 7 instead of into the vaporizer 5. Advantageously, the conduit 6 is upwardly spaced from the conduit 4 so that a height differential, indicated at 8, exists between the conduits 4 and 6. The liquid medium is permitted to flow through the adsorber 3 until the adsorption capacity of the adsorption agent has been attained.

In order to reactivate or regenerate the adsorption agent, that is, in order to remove the adsorbed impurities therefrom, the control elements for the system are now moved to assigned positions either by hand or pneumatically. The valves 17 and 18 are closed. The purified liquid medium in the vaporizer 5 is heated by means of a heat-exchanger 20 located in the vaporizer 5 and which is supplied with hot vapor via a valve 9. The vapor supplied to the heat-exchanger 20 leaves the latter via a conduit 21. The lower portion 20a of the heat-exchanger 20 brings the liquid medium to boiling whereas the upper portion 20b of the heat-exchanger 20 insures that the wet vapor thus produced is dried, that is, the upper portion 20b of the heat-exchanger 20 insures that the vapor thus produced is somewhat superheated.

The pressure-regulating valve 10 is manipulated so as to hold the closed system under the pressure necessary to maintain a desired reactivation or desorption temperature. The vaporized medium flows from the vaporizer 5 to the adsorber 3 via the conduit 4 and condenses in the adsorber 3. Condensation of the vaporized medium in the adsorber 3 continues until the heat of condensation given off brings the entire adsorption agent to the boiling temperature of the medium. The direction of flow of the medium through the adsorber 3 at this time is indicated by the downwardly pointing arrows. Upon leaving the adsorber 3, the medium, which at least in part removes adsorbed impurities from the adsorption agent, flows through the valve 10 and a conduit 11 into a separating vessel or separator 12. Initially, the medium leaving the adsorber 3 is in liquid phase, although after a period of time the medium leaving the adsorber 3 is in its gaseous state. In the illustrated embodiment, the separator 12 constitutes a continuous cooler and is provided with a heat-exchanger 22 into which a cooling fluid is introduced from a conduit 13 and through a valve 14. The cooling fluid leaves the heat-exchanger 22 via a conduit 23. When the mixture of medium and desorbed impurities, i.e. the impurities removed from the adsorption agent by the medium, leaving the adsorber 3 enters the separator 12, the desorbed impurities are able to segregate from the mixture and may settle to the bottom of the separator 12, whereas the wet medium is conveyed to the container 1 via an overflow pipe 15 in vapor form. The directions of movement of the medium and the impurities in the separator 12 are respectively indicated by the upwardy and downwardly pointing arrows. The interface between the medium and the impurities may, in known manner, be determined by means of gauge glass controls or by means of a floating valve. The impurities at the bottom of the separator 12 may, upon reaching a predetermined level, be removed from the separator 12 via a conduit 16.

It is pointed out that the capacity of the vaporizer 5 may, from case to case, be so selected, that the vapor generated from the purified medium contained therein is sufficient to reactivate the adsorption agent.

The adsorber 3 and the vaporizer 5 together define a unit for adsorption of impurities from a medium and for regeneration of the absorption agent. In order to permit substantially continuous purification of media, it is advantageous to have two or more such units arranged in parallel so that, while the adsorption agent in one of the units is being reactivated, purification of a medium may proceed in another unit. Such an arrangement is schematically illustrated in FIG. 1 by the conduit 2' and the valve 17', the conduit 2' extending from the container 1 to a non-illustrated arrangement similar to the one shown in this figure.

Figure 2:
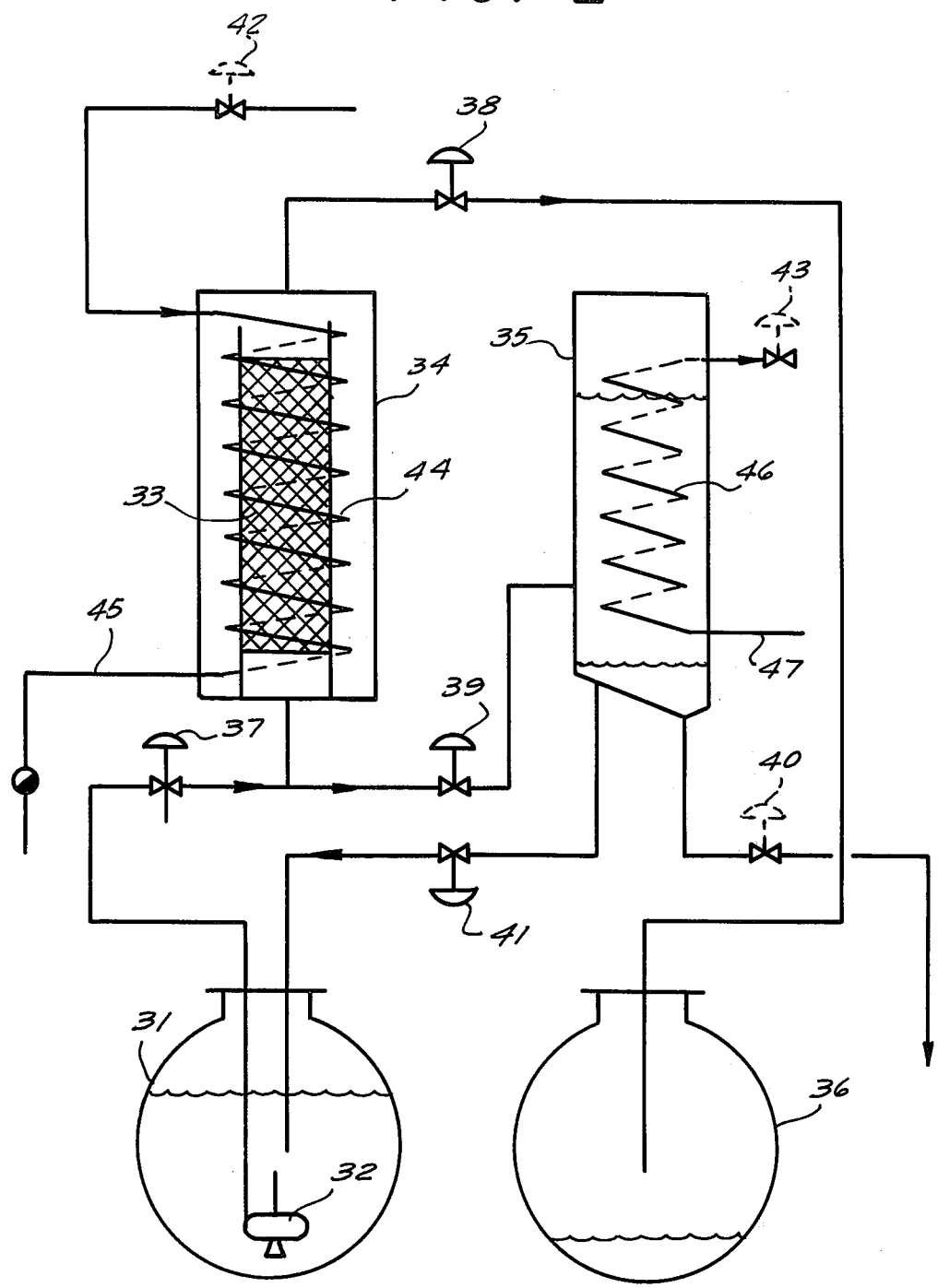
FIG. 2 is a schematic illustration of another form of arrangement for carrying out the process according to the invention.

As an example, the process of the invention will now be described with reference to the drying of liquid toluene in conjunction with FIG. 2 of the drawing. Toluene having a moisture content of 0.062% is confined in a container 31. A pump 32 conveys the toluene from the container 31 to an adsorption bed or layer 33 via a valve 37, the toluene entering the adsorption bed 33 from the bottom thereof. The adsorption agent provided in the adsorption bed 33 is the microfilter Uetion having a pore size of about 4 angstroms and a particle size between about 1 and 2 millimeters. The adsorber 33 is accommodated within a vessel 34 which is designed as a boiler or vaporizer.

The toluene initially leaving the adsorber 33 has a moisture content of less than 0.003%. The toluene leaving the adsorber 33 first fills the vessel 34, that is, the volume defined between the walls of the vessel 34 and the adsorber 33. After the vessel 34 has been filled with liquid toluene, toluene continues to flow through the adsorber 33 but now leaves the combined aggregate of adsorber-vaporizer via a valve 38 to flow into a container 36.

When the H$_2$O concentration of the dried toluene amounts to 0.007%, the total H$_2$O charge of the microfilter amount to about 18%. The valves 37 and 38 are closed.

In order to desorb the microfilter, the steam valve 42 is opened so that hot vapor is introduced into a heat-exchanger 44 located within the vessel 34, the vapor leaving the heat-exchanger 44 via a conduit 45. The valve 39 is pressure-regulated in order to obtain a pressure of about 2100 torr. The toluene in the vessel 34 is vaporized and, as a result, a zone of toluene vapor is produced in the volume defined between the walls of the vessel 34 and the adsorber 33. This toluene vapor moves downwardly through the adsorber 33 enmasse when the heat supplied by the hot vapor passing through the heat-exchanger 44 is no longer being used for heating and desorption.

The quantity of toluene provided in the vessel 34 is entirely adequate for desorbing or regenerating the microfilter. After leaving the adsorber 33, the toluene which was provided in the adsorber 33 and the vessel 34 flows through the valve 39 into a cooling vessel 35 which accommodates a heat-exchanger 46. Cooling medium enters the heat-exchanger 46 via a valve 43 and leaves the same via a conduit 47. The moisture which was originally present in the toluene before drying is now present in the cooling vessel 35 in high concentration and, through cooling, is for the most part segregated from the toluene. After the moisture of water droplets have united at the bottom of the cooling vessel 35, the water is removed from the latter by opening the valve 40. The condensed toluene remaining in the cooling vessel 35, which has a moisture content of less than 0.062%, is conveyed to the container 31 via the valve 41.

The microfilter has a residual H$_2$O charge of about 2.5%. After a cooling off period, a fresh quantity of toluene is conveyed into the microfilter for drying and a new cycle is carried out.

It will be understood that each of the elements described above, or two or more together, may also find a useful application in other types of processes and constructions differing from the types described above.

While the invention has been illustrated and described as embodied in an adsorption process and arrangement, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications wihout omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claim:

1. An arrangement for the adsorptive purification of fluids and for the regeneration of the adsorption medium, comprising an adsorption agent; means for contacting a fluid which is convertible between a liquid and a gaseous state with said adsorption agent while said fluid is in one of said states so as to permit impurities from said fluid to be adsorbed and retained by said adsorption agent; and means for converting a portion of the purified fluid from said one state to the other of said states, said converting means and said adsorption agent being in communication during adsorption and conversion thereby permitting said portion of said purified fluid to flow from said adsorption agent to said converting means during the adsorption of impurities from said fluid for conversion of said portion of said purified fluid, and permitting said portion of said purified fluid to flow from said converting means to said adsorption agent subsequent to said conversion for the removal of adsorbed impurities from and regeneration of said adsorption agent by said portion of said purified fluid, wherein said adsorption agent is accommodated in said converting means.

* * * * *